United States Patent [19]

Abela et al.

[11] Patent Number: 5,061,265

[45] Date of Patent: Oct. 29, 1991

[54] LASER TREATMENT APPARATUS AND METHOD

[75] Inventors: George S. Abela; Stephan E. Friedl, both of Gainesville, Fla.

[73] Assignee: University of Florida, Gainesville, Fla.

[21] Appl. No.: 368,655

[22] Filed: Jun. 20, 1989

[51] Int. Cl.$^5$ ............................................. A61B 17/36
[52] U.S. Cl. .......................................... 606/7; 606/15
[58] Field of Search ............................... 128/395–398, 128/303.1; 606/2, 7, 13–17, 20–28; 604/95, 96; 350/96.1, 96.26

[56] References Cited

U.S. PATENT DOCUMENTS

| | | |
|---|---|---|
| 1,791,794 | 2/1931 | Chesney . |
| 4,273,109 | 6/1981 | Enderby . |
| 4,445,892 | 5/1984 | Hussein et al. . |
| 4,448,188 | 5/1984 | Loeb .................................. 606/15 X |
| 4,512,762 | 4/1985 | Spears . |
| 4,551,129 | 11/1985 | Coleman et al. . |
| 4,592,353 | 6/1986 | Daikuzono . |
| 4,612,938 | 9/1986 | Dietrich et al. . |
| 4,646,737 | 3/1987 | Hussein et al. . |
| 4,660,925 | 4/1987 | McCaughan, Jr. . |
| 4,662,368 | 5/1987 | Hussein et al. . |
| 4,669,467 | 6/1987 | Willett et al. . |
| 4,672,961 | 6/1987 | Davies . |
| 4,676,231 | 6/1987 | Hisazumi et al. . |
| 4,681,104 | 7/1987 | Edelman .......................... 128/390 X |
| 4,693,244 | 9/1987 | Diakuzono . |
| 4,693,556 | 9/1987 | McCaughan, Jr. . |
| 4,740,047 | 4/1988 | Abe et al. ........................ 350/96.15 |
| 4,784,132 | 11/1988 | Fox et al. ................................. 606/7 |
| 4,799,479 | 1/1989 | Spears . |
| 4,800,876 | 1/1989 | Fox et al. . |
| 4,832,024 | 5/1989 | Boussignac et al. ..................... 606/7 |
| 4,832,043 | 5/1989 | Murphy-Chutorian et al. ... 128/398 X |
| 4,850,351 | 7/1989 | Herman et al. ................... 604/21 X |
| 4,860,743 | 8/1989 | Abela ..................................... 606/7 |

FOREIGN PATENT DOCUMENTS 2826383 12/1979 Fed. Rep. of Germany .

OTHER PUBLICATIONS

"Dosimetry of Plaque Ablation Using Thermal and Thermal-Optical Probe Systems", Hoffman et al, SPIE, vol. 1067, *Optical Fibers in Medicine IV*, 1989.
"Evaluation of Optical Properties and Laser Effects on Arterial Tissue Using a Microlens Tipped Optical Fiber"—Barbieri et al, SPIE vol. 713, *Optical Fibers in Medicine II*, 1986.

(List continued on next page.)

Primary Examiner—Robert A. Hafer
Assistant Examiner—Kerry Owens
Attorney, Agent, or Firm—Kerkam, Stowell, Kondracki & Clarke

[57] ABSTRACT

An apparatus for performing ablation upon a patient using laser energy. The apparatus advantageously provides for a laser beam to directly strike the tissue of a patient by having the laser beam pass out an opening in an outer hood. To prevent the apparatus from becoming fouled by burnt red blood cells or other materials, flushing solution is fed under pressure into the interior of the outer hood so as to flow out through the opening. The outer hood may include a plurality of openings and the apparatus may emit more than one laser beam, each laser beam going through a corresponding opening and having the flushing solution provided through the same opening such that the flushing is advantageously provided directly at the location where it is needed. Additionally, an auxiliary opening may be provided without any corresponding laser beam, the auxiliary opening allowing flushing solution to exit therfrom so as to stabilize the positioning of the apparatus within the vessel or other part of the patient. The apparatus includes an optical fiber having a prism which is integral with the optical fiber and used to direct the laser energy in the desired direction. A method of making the apparatus provides for the formation of the prism from the optical fiber.

24 Claims, 3 Drawing Sheets

OTHER PUBLICATIONS

"Laser Angioplasty with Angioscopic Guidance in Humans", George S. Abela et al, *Journal of the American College of Cardiology,* vol. 8, No. 1, Jul. 1986:184–92.

"Lasers in Medicine and Surgery", Council on Scientific Affairs, *Journal of the American Medical Association,* Aug. 15, 1986, vol. 256, pp. 900–907.

"Transvascular Argon Laser–Induced Atrioventricular Conduction Ablation in Dogs", George S. Abela et al, *Abstracts on the 56th Scientific Sessions,* III–145, 1983.

"The Effect of Laser Radiation on Atheromatous Plaques: A Preliminary Report", G. Abela, M.D. et al., *The American Journal of Cardiology,* Mar. 1982, vol. 49.

"Use of Laser Radiation to Recanalize Stenosed Arteries in a Live Animal Model", George Abela et al, *Abstracts,* Circulation vol. 66, Supp II, Oct. 1982.

"Laser Recanalization", George S. Abela, *Cardiovascular Disease and Chest Pain,* vol. 3, No. 4, Nov. 1987.

"Effects of Carbon Dioxide, Nd–YAG, and Argon Laser Radiation on Coronary Atheromatous Plaques", George S. Abela, M.D. et al, *The American Journal of Cardiology,* Dec. 1982, vol. 50, pp. 1199–1205.

"Laser Recanalization of Occluded Atherosclerotic Arteries in Vivo and in Vitro," George S. Abela, M.D. et al., *Circulation,* vol. 71, No. 2, Feb. 1985, pp. 403–411.

"The Healing Process in Normal Canine Arteries and in Atherosclerotic Monkey Arteries After Transluminal Laser Irradiation", George S. Abela, M.D., *The American Journal of Cardiology,* vol. 56, Dec. 1, 1985, pp. 983–988.

"Development and Early Clinical Applications of a Lateral-aiming Laser Probe", Daijo Hashimoto, *Lasers in Medical Science,* vol. 2:25, 1987, pp. 25–28.

"Lasers in Biology and Medicine", edited by F. Hillenkamp, R. Pratesi and C. A. Sacchi, NATO Symposium on Lasers in Biology and Medicine, Camaiore, Lucca, Italy, Aug. 19–31, 1979, pp. 29–35.

"A Multifiber Catheter with an Optical Shield for Laser Angiosurgery", R. M. Cothren et al, *Lasers in the Life Sciences* 1 (1), 1986, pp. 1–12.

"Hot Tip": Another Method of Laser Vascular Recanalization, George S. Abela, M.D. et al, *Lasers in Surgery and Medicine,* 5:327–335 (1985).

"Percutaneous Laser Recanalization of Totally Occluded Human Peripheral Arteries: A Technical Approach"–George S. Abela et al, *Dynamic Cardiovascular Imaging;* vol. 1, No. 4; pp. 302–308; 1988.

"Dosimetry of Plaque Ablation Using Thermal and Thermal–Optical Probe Systems", Ross. G. Hoffman et al, *SPIE* vol. 1067–*Optical Fibers in Medicine IV* (1989), pp. 120–126.

LASER TREATMENT APPARATUS AND METHOD

CROSS - REFERENCE TO RELATED APPLICATIONS

The present invention relates to improvements and/or modifications of prior U.S. application Ser. No. 056,878, now U.S. Pat. No. 4,860,743, entitled "LASER METHOD AND APPARATUS FOR THE RECANALIZATION OF VESSELS AND TREATMENT OF OTHER CORONARY CONDITIONS" filed June 3, 1987 in the name of George S. Abela. That application was a continuation in part of U.S. application Ser. No. 924,292 filed Oct. 27, 1986 as a continuation of U.S. application Ser. No. 757,778 filed July 24, 1985 which was a continuation of U.S. application Ser. No. 559,722 filed Dec. 9, 1983. Those applications, which are now abandoned (except U.S. Ser. No. 056,878) and which are assigned to the assignee of the present application, are hereby incorporated by reference.

BACKGROUND OF THE INVENTION

This invention relates to an apparatus for treating vascular conditions with high power light beams such as lasers and a method of making such an apparatus.

The use of laser beams for treatment of medical conditions has been well known. Various devices have also been developed for application of laser energy to tissue inside of a patient.

In order to provide laser energy to tissue within a patient for such purposes as ablation of plaque from the walls of a blood vessel, a technique is required which can accurately apply the laser energy to the tissue. If the laser energy is supplied to within the patient by an optical fiber and the optical fiber leads to an optical system which directs the laser beam in the appropriate direction and through a glass hood, several problems are encountered. In particular, the laser passing through the glass window may cause the build up of burnt tissue or burnt red blood cells at and around the point at which the laser exits the glass window. This black, carbonized material would in turn absorb the laser radiation before it could strike the tissue and would block or partially block proper operation of the device. The heat would be absorbed by the glass window enclosing the fiber and would be dissipated in the surrounding tissues and fluids. Depending upon the power which is used, the glass may heat faster than the surrounding fluids can dissipate the heat and this could result in permanent damage to the glass window and the hood of which it is a part. A layer of carbon may be fused to the glass rendering the device inoperable. Alternatively, the hood itself may shatter or break loose from a catheter to which it is attached. Although the catheter may be useful at providing an optically clear flushing solution (usually saline), the solution is often not supplied to the location where it is most needed. Moreover, even if one were to displace the blood between the glass hood and the tissue with an optically clear solution such that the laser beam may properly irradiate the tissue and prevent the build up of burnt red blood cells on the hood, burnt tissue may still accumulate on the hood if it contacts the tissue. Further, such a technique would not be useful if the regions surrounding the tissue which is being subjected to laser energy cannot be cleared of blood, as is the case when one wants to perform ablation on the His bundle in the ventricular septum of the heart.

2

Although high temperature resistant glasses may be employed to increase the survivability of a glass hood, this still does not avoid the problem of blockage of the laser radiation and build up of heat o the hood.

A further danger of using a glass window or glass hood is that the glass might break, even if the blockage and heat build up problems are avoided. Breakage of such a glass hood would allow shards of glass into a patient This is especially dangerous in that glass is not x-ray opaque so that the pieces of glass would not be visible by fluoroscopic examination.

A further complicating factor in providing safe and effective ablation is that one must provide an optical system which is relatively simple and which has the ability to carry relatively high power densities.

OBJECTS AND SUMMARY OF THE INVENTION

Accordingly, it is a primary object of the present invention to provide a new and improved laser treatment apparatus and method of making such a laser treatment apparatus.

A more specific object of the present invention is to provide such an apparatus which avoids the problem of blockage of the laser beam.

Yet another object of the present invention is to provide such an apparatus which minimizes or avoids any heat build up upon glass members.

A still further object of the present invention is to provide a device which minimizes the risk that pieces of glass could injure a patient.

Yet another object of the present invention is to provide an apparatus which improves one's ability to properly position the apparatus such that the laser beam is directed towards the proper location.

A still further object of the present invention is to provide such an apparatus which will work with a relatively simple optical system.

Another object of the present invention is to provide an advantageous method of constructing such an apparatus.

The above and other objects of the present invention are realized by an apparatus for heating tissue inside of a patient. As used herein, "heating tissue" shall refer to application of sufficient thermal energy to ablate or thermally damage tissue The apparatus includes an outer hood having a first opening disposed therein and an optical fiber having a tip within the outer hood. The optical fiber is operable to receive light and operable to transmit a light beam of high power (i.e., sufficient to ablate or thermally damage tissue) from the tip through the first opening. A catheter is connected to the outer hood for applying flushing solution to within the hood such that the flushing solution flows out of the first opening. Preferably, an inner hood is disposed within the outer hood, the tip being disposed within an interior of the inner hood. The interior of the inner hood is sealed to prevent flushing solution from entering therein. The light beam is disposed at an angle relative to the lengthwise direction of the optical fiber. The tip has a prism integral with the optical fiber. The prism has a generally flat slant face at an angle relative to a lengthwise direction of the optical fiber. (As used herein, a "slant face" is a surface which is neither parallel or perpendicular to the lengthwise direction of an optical fiber.) The prism may have a plurality of generally flat slant faces. The first opening is preferably on a side of the outer hood and the outer hood has a second opening opposite the first opening and operable to allow flushing solution to flow out there through The tip may also include a surface perpendicular to the lengthwise direction. Light may be transmitted from the tip through a second opening in the hood, which opening also allows flushing solution to flow out there through. First and second electrodes may be mounted outside the outer hood and are operable for detecting the presence of conductive tissue. The outer hood is made of metal, whereas the inner hood is made of glass.

The present invention may alternately be described as an apparatus having an outer hood with a first window disposed therein. (As used herein, a "window" includes an opening and a zone or area having transparent material such as glass.) An optical fiber has a tip and is operable to transmit a light beam of high power from the tip through the first window for application to tissue of a patient. A catheter is connected to the outer hood for applying flushing solution adjacent to the tissue subjected to the light beam. The tip has a prism integral with the optical fiber and the prism has a first slant face in a particular embodiment. In that embodiment, the prism is operable to transmit a light beam of high power through the first window. A second window in the outer hood may be used in conjunction with a second slant face in the tip in a particular embodiment. The outer hood may include a third window and the prism may include a flat third face such that the prism may transmit a light beam of high power through the third window. Each of the windows is an opening and the catheter is connected to supply flushing solution to within the outer hood such that the flushing solution flows out of the windows. In one embodiment, the second face is between 85° and 95° relative to the lengthwise direction of the optical fiber and the second window is at an end of the outer hood. An inner hood is disposed within and anchored to the outer hood and the tip is disposed within an interior of the inner hood. The interior of the inner hood is sealed to prevent flushing solution from entering therein.

The method of making an apparatus according to the present invention comprises the steps of placing a tip of an optical fiber adjacent a barrier, transmitting laser energy through the optical fiber and out from the tip to hit the barrier until the tip has melted, halting transmission of laser energy such that the tip solidifies as a generally spherical portion, grinding a generally flat slant face in the tip, anchoring the optical fiber to an outer hood such that light passing out of the tip will pass through a first window in the outer hood, and securing a catheter to the outer hood such that the catheter is positioned to supply flushing solution to adjacent to the outside of the first window. The anchoring step is accomplished by securing the optical fiber to an inner hood and securing the inner hood to the outer hood. The method further comprises the step of cutting an opening in the outer hood, the opening serving as the first window.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
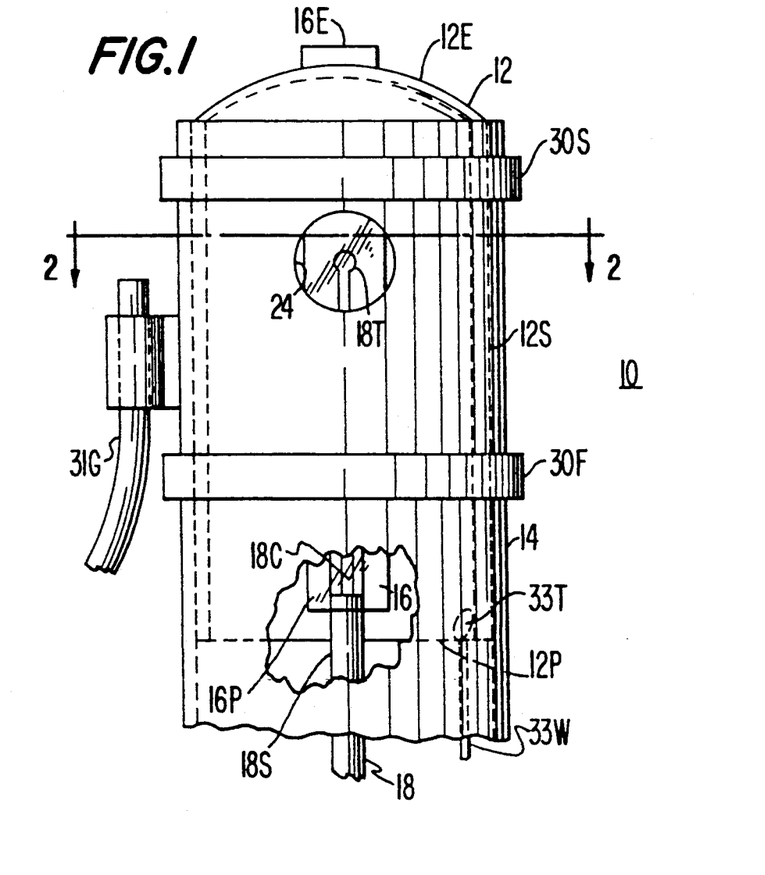
FIG. 1 shows a side view of a first embodiment apparatus according to the present invention with some parts broken away.

As shown in FIG. 1, a first apparatus 10 according to the present invention includes an outer hood 12 having an end portion 12E and a cylindrical side wall 12S. Although end 12E is shown curved, it could alternately be flat. The outer hood 12, which is open at an end opposite end 12E, has a catheter 14 secured to it around the outside of sidewall 12S.

Disposed within the outer hood 12 is an inner hood 16 which is a glass tube extending from just above the open end 12P of outer hood 12 up to end flush with or slightly above the end cap 12E where an end portion 16E extends in and is secured to a cylindrical hole centrally located within end 12E. The end 16E of inner hood 16 is closed and the inner hood 16 extends lengthwise in parallel and centrally within the cylindrical sidewall 12S of outer hood 12.

The end 16P of inner hood 16 is open so as to accommodate an optical fiber 18 having a protective coating and cladding (collectively labeled 18S) which is removed to provide an uncladded core 18C extending centrally and parallel to the inner hood 16. (The optical fiber cladding is not always removable. In the case of plastic clad fibers, the cladding may be removed. Glass clad fibers, however, cannot have their cladding stripped. In general, if the cladding is flammable, as is the case with plastic clad fibers, it is removed, otherwise the cladding is left intact. The buffer coat is always removed.) A short length of the covering and cladding may extend into the tubular inner hood 16 and be adhesively attached thereto so as to prevent flushing liquid provided by catheter 14 from entering into the inner hood 16. Alternately, the inner diameter of the hood 16 can be smaller than the outer diameter of coating/cladding 18S and the coating/cladding 18S may be glued to abut and seal against the lower surface of end 16P to prevent flushing solution from entering into hood 16. The core 18C extends up to a tip 18T, the structure of which will be discussed below. The tip 18T serves to emit a laser beam upon a laser beam entering an end of optical fiber 18 remote from the tip 18T, the remote end being outside of a patient into which the apparatus 10 may be inserted.

Figure 2:
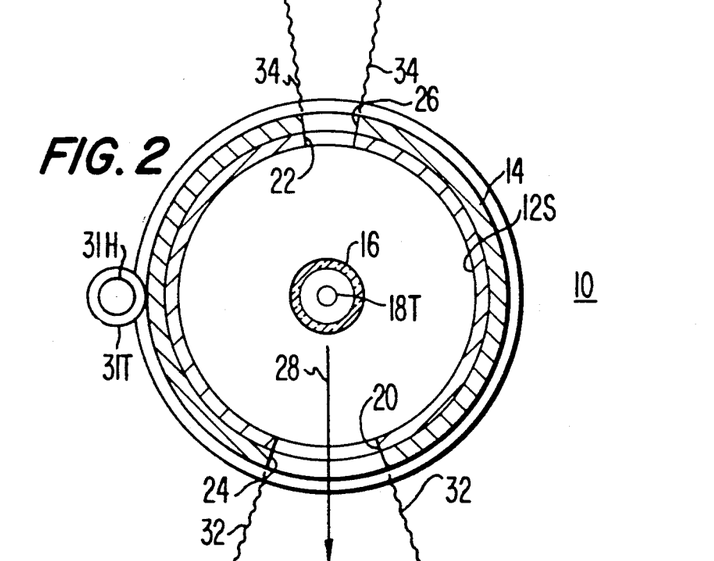
FIG. 2 shows a cross section view taken along lines 2-2 of FIG. 1.

Continuing to consider FIG. 1, but also considering the cross section view of FIG. 2, a first window 20 is an opening disposed in the sidewall 12S, whereas a second opening 22 is disposed in wall 12S opposite the first opening 20. The openings 20 and 22 in wall 12S are respectively in registry with corresponding openings 24 and 26 in the catheter 14. The openings 20, 22, 24, and 26 are disposed about the axial location of the tip 18T such that a laser beam 28 (28 representing the central axis of the beam in accord with standard conventions in the optical field) emitted by tip 18T perpendicular to the lengthwise direction of optical fiber 18 passes through openings 20 and 24 as shown in FIG. 2.

Optional first and second electrodes 30F and 30S (FIG. 1 only) may be disposed upon the device if it is to be used for His bundle or arrhythmia foci ablation. Under those circumstances, the electrodes 30F and 30S, each of which is a cylindrical band, would be connected to electrical conduction leads (not shown) which extend through the catheter 14 to an electrocardiographic monitor (not illustrated) for detection and localization of the conduction tissue.

An optional tube 31T having hole 31H may accommodate a guidewire 31G (partially shown) to provide guidewire control of the device, especially when dealing with coronary arteries. An optional thermocouple 33T and wire 33W (FIG. 1 only) could be used to monitor temperature in the probe and to predict possible failure of the probe.

The basic operation of the present invention is relatively straightforward. The device 10 is inserted into the patient using known techniques until the tip 18T is positioned such that the laser beam 28 will fall upon the tissue which is to be ablated. An angioscope or fluoroscopy may be used to properly position the apparatus relative to the tissue which is treated. Flushing solution is fed into the catheter 14 from an end (not shown) outside of the patient. The flushing solution enters the interior of the outer hood 12 by way of the open end 12P. The flushing solution then leaves the interior of the outer hood 12 by way of the openings 20, 22, 24, and 26. More specifically, and as best shown in FIG. 2, a flow of flushing solution exits the openings 20 and 24 generally along the boundaries indicated by lines 32, whereas a flow of flushing solution exits the openings 22 and 26 generally along the lines 34. The flushing solution does not enter the inner hood 16 because this inner hood, which is made of glass, is sealed by a portion of optical fiber 18. After the flushing solution is flowing out the openings, a laser source (not shown) transmits a high energy laser beam from an end of the optical fiber 18 remote from tip 18T to the tip 18T. The tip 18T directs the laser beam in a manner discussed in more detail below such that the laser beam exits out the openings 20 and 24, the laser beam 28 initially passing through the glass hood 16.

Significantly, the flushing solution will provide a clear field for the laser beam 28. By forcing the flushing solution through the opening corresponding to 20 and 24, there is no contact between the tissue of the patient and either the outer hood 12 or inner hood 16 at the point of laser emission. Because flushing solution is being supplied under pressure through catheter 14 to the interior of outer hood 12, burned red blood cells and other tissue is not allowed to contact the inner hood 16. This avoids having the hood 16 become fouled by burnt red blood cells or other tissue. The arrangement further advantageously provides for continuous cooling of the tip of the probe by the flushing solution.

As shown in FIG. 2, the central axis of beam 28 extends through the opening defined by 20 and 24. Additionally, this beam axis is transverse to the catheter (i.e., the length of the catheter). As also shown in FIG. 2, the arrangement provides that any portion of the apparatus through which the beam 28 passes between the tip 18T and tissue of the patient is shielded from contact with the tissue of the patient by the outer hood 14. As also shown in FIG. 2, light from the beam 28 necessarily passes first through the flushing solution within the outer hood 12 and then through the opening 20 before is strikes tissue of the patient.

Advantageously, the clear field provided by the openings 20 and 24 is small and directional in nature such that the entire body cavity in which the laser application is taking place need not be cleared. As the flow of flushing solution out openings 20 and 24 may cause the probe or apparatus 10 to tend to move away from the tissue which is being subjected to laser 28, the back openings 22 and 26 provide an opposing stream of flushing solution corresponding to lines 34 in FIG. 2 so as to maintain the apparatus 10 steady against such force caused by the flushing solution at lines 34. Various modifications could be made in the openings 22 and 26 so as to maximize this stabilizing force. In the illustration of FIG. 2, the openings 22 and 26 are shown smaller than the openings 20 and 24 such that the pressurized fluid exiting along lines 34 will be at a higher velocity than that exiting along lines 32. By providing greater acceleration of fluid through openings 22 and 26 and therefore greater force opposite the direction of laser beam 28, the design helps to stabilize the probe or apparatus 10 against the tissue which is being treated.

The design is also quite helpful at minimizing danger to the patient from the glass inner hood 16. Specifically, the cooling by forcing of the flushing solution in the space between the inner hood 16 and the outer hood 12 allows the probe to project more energy with less risk of shattering the glass hood 16 due to high temperatures. Further, the outer hood 12, which preferably is made of stainless surgical steel, should capture shards of glass in the event that the glass hood 16 somehow does break. Note that the upper end 16E of glass hood 16 would be glued to the end cap 12E such that it is quite unlikely that portion 16E would release pieces of glass into the patient. (High temperature epoxy is used for gluing the fiber 18 to the inner hood 16 and the inner hood 16 to the outer hood.) As the outer hood 12 is made of metal, this provides a superior thermal monitoring capacity such that one may attach a temperature sensor such as thermocouple 33T to the hood 12. Unlike a glass hood, a metal hood such as 12 will tend to avoid having particular hot spots. That is, a good thermal conductor such as metal hood 12 will more evenly distribute the heat throughout the probe and a temperature sensor such as thermocouple 33T at one location on the hood 12 allows one to relatively accurately gauge the overall heat of the device. In contrast to the ease with which a thermocouple may be spotwelded directly to the metal hood 12, it is quite difficult to securely attach a thermocouple or other temperature monitoring device to glass.

Although the use of a second opening corresponding to 22 and 26 opposite the first opening corresponding to 20 and 24 is highly advantageous, it is noted that the inclusion of openings at 22 and 26 is not required to realize several of the broad concepts of the present invention.

Figure 3:
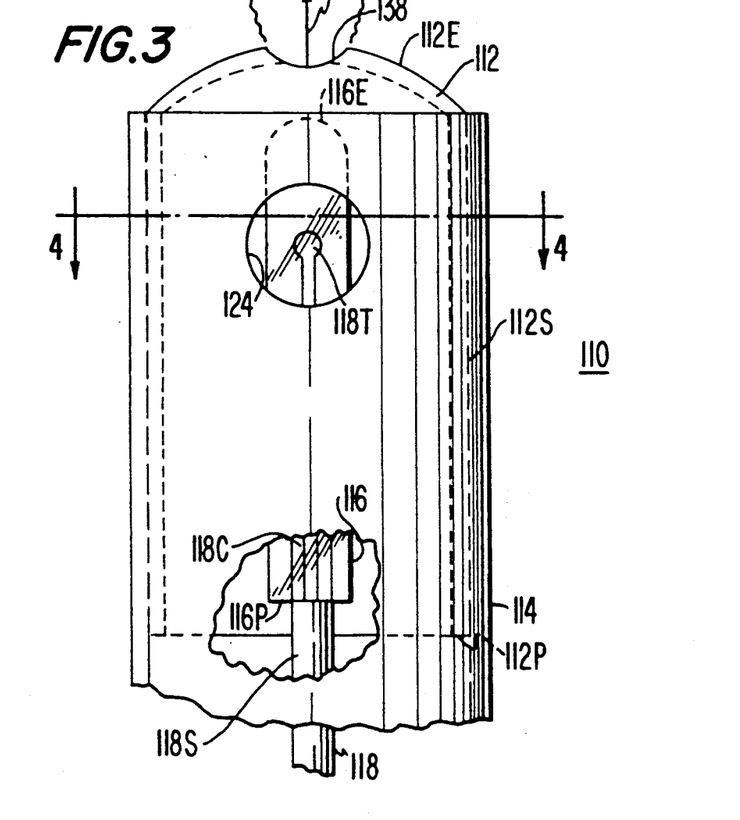
FIG. 3 shows a side view of a second embodiment apparatus with a portion broken away.
Figure 4:
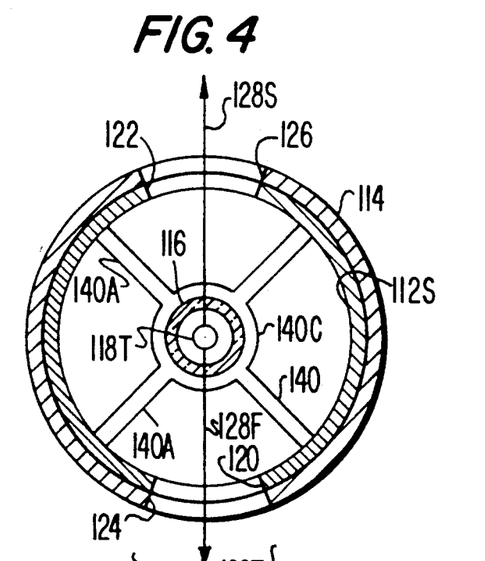
FIG. 4 shows a cross section view taken along lines 4-4 of FIG. 3.

With reference now to FIGS. 3 and 4, a second embodiment of the apparatus according to the present invention is illustrated. The apparatus 110 of FIGS. 3 and 4 has numerous similarities to the apparatus 10 of FIGS. 1 and 2. Accordingly, the discussion which follows will emphasize the differences. Components within the apparatus 110 are labeled in the 100 series with the same last two numerals (and letter if any) as the corresponding component in the embodiment of FIGS. 1 and 2. In apparatus 110, the tip 118T is structured such that the laser beam passing along optical fiber 118 will be split three ways. The tip 118T will emit a first laser beam 128F through a first opening corresponding to 120 and 124 and a second laser beam 128S corresponding to openings 122 and 126. In the arrangement of FIGS. 2 and 3, each of the openings 120, 122, 124, and 126 may be of the same size. A third laser beam 128T (FIG. 3 only) is emitted from a cylindrical hole 138 disposed centrally within the end cap 112E.

As best shown in FIG. 3, the upper end 116E of inner hood 116 (which is a glass tube) does not extend up to the end cap 112. Instead, the upper end 116E is simply closed off (as by fusing an end of the tube of glass). Because the end 116E does not reach up to the end 112E of outer hood 112, a support 140 is used to secure inner hood 116 to outer hood 112. In particular, the support 140 includes a center cylindrical hub 140C which extends around and is secured to a portion of inner hood 116. Radiating out from the cylindrical 140C are four arms 140A which are secured to the inner surface of sidewall 112S of outer hood 112. As an alternative to the support 140, the inner hood 116 could simply be glued to the outer hood 112 by placing a large amount of epoxy in the gap there between. One would leave openings in the epoxy or later make openings in the epoxy so as to insure that flushing solution from the lower end (relative to the positioning of FIG. 3) of catheter 114 may enter into the zone between inner hood 116 and outer hood 112.

The arrangement of FIG. 3 and 4 is advantageous in allowing one to effectively treat completely occlusive atherosclerotic lesions. In particular, the apparatus 110 is pushed into a vessel until the end cap 112E is adjacent the blockage, whereupon the flushing solution is supplied so as to exit out the front and back openings corresponding to laser beams 128F and 128S and out the end opening 138 corresponding to laser beam 128T. The laser beam 128T will hit the blockage and will remove the blockage such that the probe 110 can be further inserted until the beam 128F and 128S can fall upon the portion of the blockage which remains following treatment by laser 128T. Note that the tip 118T could alternately be arranged to supply a laser beam corresponding to 128F and laser beam 128T, without providing the laser beam corresponding to 128S. The arrangement for the tip 118T will be discussed in more detail below.

The manner of assembling the devices 10, and 110 is relatively straightforward. Initially, the inner hood such as 16 is constructed as a cylindrical tube of glass with one end closed. The protective cover and cladding of a portion of an optical fiber is removed and the tip of the fiber is constructed according to a process discussed in detail below. The fiber such as fiber 18 in FIG. 1 is then secured to the inner hood 16. As discussed above, the inner hood 16 may have an inner diameter to just accommodate the core such as 18C and epoxy may be disposed around the periphery of the protective cover and cladding 18S to seal the inner hood 16. In that event, the protective cover and cladding 18S will be disposed outside of the opening 16P and immediately at that opening. Alternately, and as shown in FIG. 1, a small portion of the cladding and cover 18S may extend into the opening 16P.

Having anchored the optical fiber 18 to the inner hood 16, and outer hood 12 having a cylindrical sidewall 12S and an end cap 12E which may be tapered (as shown) has a hole drilled centrally within the end cap 12E or the hole may be formed when the end cap 12E is formed with the outer hood 12. The inner hood 16 is then inserted into the hole in end cap 12E and glued securely in place. The outer hood 12 is then heated and slid into an elastic catheter 14 and is securely held in place by catheter 14 upon its cooling. If the device is to be used for his bundle ablation, electrode bands 30F and 30S may be secured around the outside of the catheter 114 and attached to wires by way of holes (not shown) extending through catheter 14 and hood 12. The holes corresponding to openings 20, 22, 24, and 26 may be made by drilling or otherwise in the catheter 14 and outer hood 12. (The holes or openings 20 and 22 in outer hood 12 may be drilled before the inner hood 16 is secured thereto and, following the placement of the catheter 14 around the outer hood 12, the resilient material of the catheter may simply be cut to realize openings 24 and 26.)

The construction of the arrangements of FIGS. 3 and 4 is basically the same as discussed above, except that the inner hood 116 is secured to the outer hood 112 by the support 140 or alternately by glue with holes formed in an epoxy layer to insure that flushing solution may flow into the outer hood.

Figure 5:
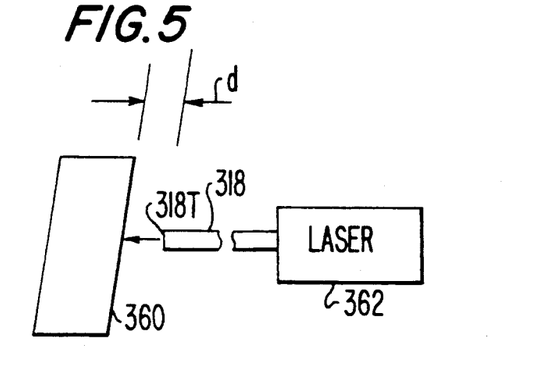
FIG. 5 is a schematic illustrating part of the process of making a prism at a fiber optic tip according to the present invention.

With reference now to FIG. 5, the process of making the tip, such as tip 18T or 118T will be discussed. Initially, it should be noted that the optical fiber tips according to the present invention includes a prism integral with the optical fiber, meaning that the prism is not made from a separate piece of material attached to the optical fiber.

Figure 6:
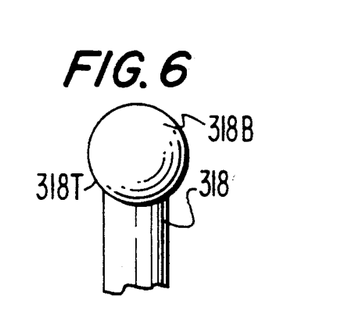
FIG. 6 shows a side view of a fiber optic tip as produced by the step of FIG. 5.

As shown in FIG. 5, an optical fiber 318 is placed a short distance d (preferably one millimeter or less) from a brick 360 and laser energy is supplied by laser 362 (which may be a Nd - YAG laser). The laser energy is applied to the brick which reradiates infrared energy or heat so as to melt the tip 318T. If desired, the optical fiber 318 may be arranged vertically during this operation. After the tip 318T has melted sufficiently, the laser 362 is turned off and the tip 318T solidifies in a generally spherical ball-like shape 318B as shown in FIG. 6.

Figure 7:
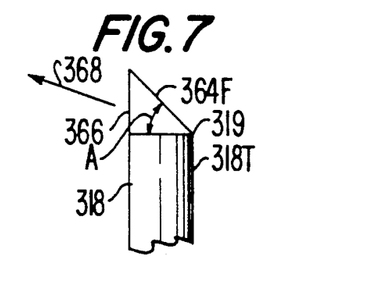
FIG. 7 shows a side view of a first embodiment fiber optic tip which may be made from the tip of FIG. 6.

Once the ball 318B has solidified, a generally flat first slant face 364F (see FIG. 7) is established in the tip 318T by subjecting the portion 318B to grinding on a glass grinding wheel (not shown). The slant face 364F could have various angles, but preferably will have an angle A of about 60° to a plane (not shown) perpendicular to the central axis of fiber 318. Additionally, a generally flat surface 366 is established by grinding in a direction generally parallel to the lengthwise direction of the optical fiber 318. The surface or face 366 may be ground out before the face 364F is ground out. As shown in FIG. 7, the tip 318P has a prism formed integrally therewith by virtue of the surfaces 364F (at 45° relative to the fiber axis) and 366 which are ground into the tip such that, upon applying a laser beam to a remote end (not shown) of optical fiber 318, the laser energy passing through optical fiber 318 will be emitted from tip 318T in a direction corresponding to arrowhead 368 in FIG. 7. This direction may be perpendicular to the lengthwise direction of the optical fiber 318 or, as shown, have a slight forward component.

Upon completing the construction of the tip 318T in the manner shown in FIG. 7, the optical fiber may be mounted within a glass inner hood such as 16 or 116 as discussed in detail above and the overall apparatus may be constructed using the steps discussed above. It should be noted that the tip 318T emits laser energy on only one side corresponding to the single beam emission tip l8T of FIGS. 1 and 2. Other tips may be constructed to emit laser beams in more than one direction as discussed hereafter.

Figure 8:
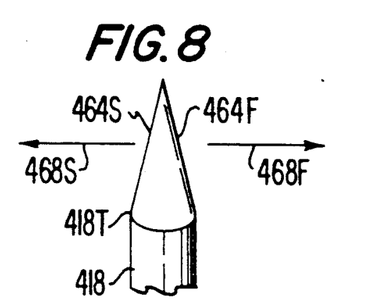
FIG. 8 shows a side view of a second embodiment fiber optic tip which may be made from the tip of FIG. 6.

As shown in FIG. 8, an alternate optical fiber 418 includes tip 418T having two generally flat slant surfaces 464F and 464S so as to emit two laser beams 468F and 468S. The surfaces 464F and 464S will be constructed according to the same process discussed above with respect to FIGS. 5-7 except that more slant surfaces will be established by the grinding process and the surfaces or faces may be at different angles. In similar fashion, various other surfaces could be cut into an optical fiber tip from a ball portion 318B in order to provide various patterns for the laser beams emitted from such tip.

Figure 9:
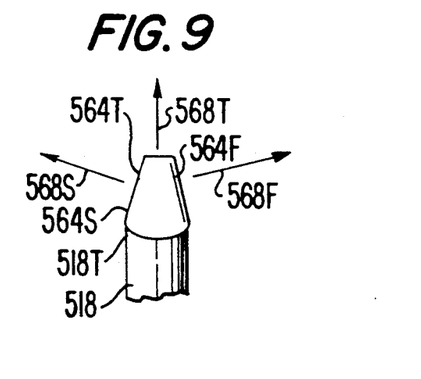
FIG. 9 shows a side view of a third embodiment fiber optic tip which may be made from the tip of FIG. 6.

In FIG. 9, slant surfaces or faces 564F and 564S are cut in tip 518T of optical fiber 518. Additionally, an end face 564T is cut between 85° and 95° relative to the lengthwise direction of optical fiber 518 and is preferably perpendicular to the lengthwise direction such that laser beam 568T will be parallel and axial to the lengthwise direction of fiber 518. Additionally, beams 568F and 568S are emitted from the tip of FIG. 9, this tip being constructed so as to generate two side beams and one end beam, this tip corresponding also to tip 118T in FIGS. 3 and 4.

Figure 10:
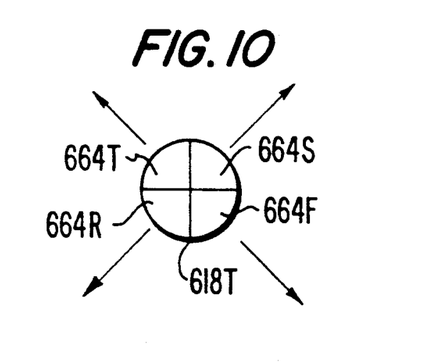
FIG. 10 shows a top view of a fourth embodiment fiber optic tip which may be made from the tip of FIG. 6.

The arrangement of FIG. 10 is a tip 118T having four slant faces 664F, 664S, 664T, and 664R in order to emit four sideways laser beams, which beams are unlabeled in FIG. 10 to avoid complicating this drawing.

From the above, it will be seen that a prism may be integrally formed with the optical fiber by using the steps discussed relative to FIGS. 5 and 6 and then cutting surfaces by using the cutting wheel in the suggested fashion. In order to have the prism at the tip of the various optical fibers operate properly, the prism should be contacting air and not contacting the flushing solution such as saline. Accordingly, the internal hood such as hood 16 in FIG. 1 is sealed to prevent the flushing solution from reaching therein.

As an alternative to using a sealed inner hood to provide total internal reflection, the present invention in its broadest aspects contemplates a single hood design using a mirror surface applied to one or more of the surfaces of an optical fiber tip. Such a single hood design could not rely on total internal reflection in the fiber tip (the double hood design uses total internal reflection) because the flushing solution would be adjacent the fiber tip. The index of refraction of the flushing solution prevents the tip from having total internal reflection for a single hood design. Instead of sealing the flushing solution by use of an inner hood, a reflective layer could direct the beam to a proper direction. The cost and difficulty in applying the reflective or mirror surface and the damaging power densities to which such a mirror would be subjected are avoided by the dual hood design.

Referring back to FIG. 7, it should be noted that the prism tip of the present invention provides an overhang portion 319 which extends out beyond the usual boundaries of the optical fiber 318. In other words, since the prism tip was fashioned from the spherical portion of FIG. 6, there will normally be an overhang portion extending beyond the edge of the optical fiber. This advantageously reduces the loss of light energy which might otherwise occur due to the stripping of the cladding. Although the overhang portion 319 is shown extending out from the slant face 364F, there would also be an overhang portion projecting out from the plane of view of FIG. 7 and projecting in to the plane of view of FIG. 7 (i.e., on the side opposite the view of FIG. 7). There may also be an overhang portion corresponding to face 366. The tips other than that illustrated in FIG. 7 would preferably also include one or more overhang portions.

Figure 11:
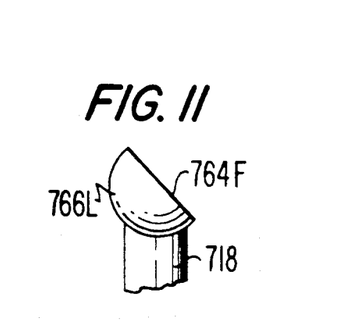
FIG. 11 shows a side view of a fifth embodiment fiber optic tip made from the tip of FIG. 6.

Although the embodiment of FIG. 7 has the flat face 366 ground therein, one could alternately provide an optical fiber 718 in FIG. 11 with the slant face 764F and without grinding a face such as 366. Instead, the remaining spherical portion 766L of FIG. 11 may function as a plano-convex lens.

Although not shown, one could grind faces similar to 366 in FIG. 7 in three of the four sides (i.e., as seen from the tip) of the ball 318B in FIG. 6 and grind 364F (FIG. 7) in the remaining side so that the prism tip has one slant face, one rectangular face and two triangular faces. Each of the faces would be flat and the resulting "squared" tip could be used to lock the fiber to projections (not shown) in the glass inner hood so that the fiber and glass hood would rotate in unison.

It should be emphasized that the present invention in its preferred form includes both the prism integral with the optical fiber and the dual hood. However, the present invention, in its broadest aspects, contemplates use of the prism-tipped fibers without necessarily using the dual hood arrangement. It should therefore be appreciated that references to an outer hood in the present application and its claims should not be interpreted as requiring an inner hood except where expressly stated. Further, the localized flushing feature (i.e., the flushing solution passes through the opening through which the laser beam is directed) and the dual hood design could be used with optical fibers which do not have the prism-tipped arrangements.

An important advantage of the present invention is that it can create a channel through an occlusive vascular lesion which is larger than the diameter of the catheter. Prior forward-only lasing systems (i.e., no side beams) are only able to match the size of the delivery catheter and reply on the mechanical effect of forcing their guiding catheter through the occlusion. These devices are usually not adequate to debulk the lesion. Advantageously, the prism-tipped fibers of the present invention generate side beams which can open a channel wider than the catheter with minimal mechanical effect. The side beams will ablate tissues several millimeters beyond the edges of the catheter. Rotating the catheter will remove tissues in a 360° ring within the vessel.

It should also be noted that the present invention may work with any type of laser. For example, argon, Nd:YAG, pulsed dye and Excimer lasers can be used.

Although the guidewire and thermocouple are shown only for a single embodiment, these features could be used on the other embodiments as well.

Although various specific instructions and designs have been shown and described herein, it is to be understood that these are for illustrative purposes only. Various modifications and adaptations will be apparent to those of skill in this art. Accordingly, the scope of the present invention should be determined by reference t the claims appended hereto.

What is claimed is:

1. An apparatus for heating tissue inside of a patient comprising:
   an outer hood having a first opening disposed therein;
   an optical fiber having a tip within said outer hood, said optical fiber operable to receive light and operable to transmit a light beam of high power with a central axis extending from said tip through said first opening; and
   a catheter connected to said outer hood for supplying flushing solution to within said outer hood such that the flushing solution flows out of said first opening; and
   further comprising an inner hood within said outer hood, said tip being disposed within an interior of said inner hood, said interior being sealed to prevent flushing solution from entering therein.

2. The apparatus of claim 1 wherein said tip is constructed such that said light beam is disposed at an angle relative to a lengthwise direction of said optical fiber.

3. The apparatus of claim 1 wherein said tip has a prism integral with said optical fiber.

4. The apparatus of claim 3 wherein said prism has a generally flat slant face at an angle relative to a lengthwise direction of said optical fiber.

5. The apparatus of claim 3 wherein said prism has a plurality of generally flat slant faces at an angle relative to a lengthwise direction of said optical fiber.

6. The apparatus for heating tissue inside of a patient comprising:
   an outer hood having a first opening disposed therein;
   an optical fiber having a tip within said outer hood, said optical fiber operable to receive light and operable to transmit a light beam of high power with a central axis extending from said tip through said first opening; and
   a catheter connected to said outer hood for supplying flushing solution to within said outer hood such that the flushing solution flows out of said first opening; and
   wherein said first opening is on a side of said outer hood and said outer hood has a second opening opposite said first opening and operable to allow flushing solution to flow out therethrough.

7. An apparatus for heating tissue inside of a patient comprising:
   an outer hood having a first opening disposed therein;
   an optical fiber having a tip within said outer hood, said optical fiber operable to receive light and operable to transmit a light beam of high power with a central axis extending from said tip through said first opening; and
   a catheter connected to said outer hood for supplying flushing solution to within said outer hood such that the flushing solution flows out of said first opening; and
   wherein said tip has a generally flat slant face at an angle relative to a lengthwise direction of said optical fiber and said tip has a surface perpendicular to said lengthwise direction.

8. An apparatus for heating tissue inside of a patient comprising:
   an outer hood having a first opening disposed therein;
   an optical fiber having a tip within said outer hood, said optical fiber operable to receive light and operable to transmit a light beam of high power with a central axis extending from said tip through said first opening; and
   a catheter connected to said outer hood for supplying flushing solution to within said outer hood such that the flushing solution flows out of said first opening; and
   wherein said first opening is on a side of said outer hood and said outer hood has an end having a second opening such that light is transmitted from said tip through said second opening, and wherein said second opening is operable to allow flushing solution to flow out therethrough.

9. An apparatus for heating tissue inside of a patient comprising:
   an outer hood having a first opening disposed therein;
   an optical fiber having a tip within said outer hood, said optical fiber operable to receive light and operable to transmit a light beam of high power with a central axis extending from said tip through said first opening; and
   a catheter connected to said outer hood for supplying flushing solution to within said outer hood such that the flushing solution flows out of said first opening; and
   further comprising first and second electrodes mounted outside said outer hood and operable for detecting the presence of conductive tissue.

10. The apparatus of claim 1 wherein said outer hood is made of metal.

11. The apparatus of claim 1 wherein all portions of the apparatus within which the light beam passes as it exits from the tip towards tissue of the patient are shielded from the tissue by the outer hood, and the light beam does not pass through the outer hood itself.

12. An apparatus for heating tissue inside of a patient comprising:
   an outer hood having a first opening disposed therein;
   an optical fiber having a tip within said outer hood, said optical fiber operable to receive light and operable to transmit a light beam of high power with a central axis extending from said tip through said first opening; and
   a catheter connected to said outer hood for supplying flushing solution to within said outer hood such that the flushing solution flows out of said first opening; and
   wherein the catheter is connected to the outer hood for supplying flushing solution between the tip and the first opening such that light from the light beam necessarily must pass first through flushing solution and then through the first opening before impacting tissue.

13. An apparatus for heating tissue inside of a patient comprising:
   an outer hood having a first window disposed therein;
   an optical fiber having a tip within said outer hood, said optical fiber operable to receive light and operable to transmit a light beam of high power with a central axis extending from said tip through said first window for application to tissue of a patient; and a catheter connected to said outer hood for applying flushing solution adjacent to tissue subjected to said light beam; and wherein said tip has a prism integral with said optical fiber and said prism has a first slant face which is generally flat and extends at an angle relative to a lengthwise direction of said optical fiber such that said central axis of said light beam is transverse to said catheter.

14. An apparatus for heating tissue inside of a patient comprising:

an outer hood having a first window disposed therein;

an optical fiber having a tip within said outer hood, said optical fiber operable to receive light and operable to transmit a light beam of high power from said tip through said first window for application to tissue of a patient;

a catheter connected to said outer hood for applying flushing solution adjacent to tissue subjected to said light beam; and wherein said tip has a prism integral with said optical fiber and said prism has a first slant face which is generally flat and extends at an angle relative to a lengthwise direction of said optical fiber; and wherein said outer hood has a second window and said prism includes a generally flat second face, and wherein said prism is operable to transmit light beams of high power through said first and said second windows.

15. The apparatus of claim 14 wherein said second face is a slant face extending at an angle relative to said lengthwise direction.

16. The apparatus of claim 15 wherein said outer hood has a third window and said prism includes a generally flat third face and wherein said prism is operable to transmit a light beam of high power through said third window.

17. The apparatus of claim 16 wherein each of said first, second, and third windows is an opening and said catheter is connected to supply flushing solution to within said outer hood such that flushing solution flows out of said first, second and third windows.

18. The apparatus of claim 14 wherein said second face is between 85° and 95° relative to said lengthwise direction and said second window is at an end of said outer hood.

19. The apparatus of claim 13 wherein said first window is an opening and said catheter is connected to supply flushing solution to within said outer hood such that flushing solution flows out of said first window, and further comprising an inner hood within and anchored to said outer hood, said tip being disposed within an interior of said inner hood, said interior being sealed to prevent flushing solution from entering therein.

20. The apparatus of claim 13 wherein said prism has an overhang portion.

21. A method of making an apparatus for heating tissue inside of a patient comprising the steps of:

placing a tip of an optical fiber adjacent a barrier;

transmitting laser energy through said optical fiber and out from said tip to hit said barrier until said tip has melted;

halting the transmission of laser energy such that said tip solidifies as a generally spherical portion;

grinding a generally flat slant face in said tip, said slant face having an angle relative to a lengthwise direction of said optical fiber; and anchoring the optical fiber to an outer hood such that light passing out of said tip will pass through a first window in said outer hood.

22. The method of claim 21 further comprising the step of: securing a catheter to said outer hood such that said catheter is positioned to supply flushing solution to adjacent to the outside of said first window.

23. The method of claim 20 wherein the anchoring step is accomplished by securing the optical fiber to an inner hood and securing the inner hood to the outer hood.

24. The method of claim 23 further comprising the step of cutting an opening in said outer hood, said opening serving as said first window.

* * * * *